United States Patent [19]

Calabria et al.

[11] Patent Number: 4,963,534

[45] Date of Patent: Oct. 16, 1990

[54] PROCESS FOR SOLUBILIZING POLYANOINIC BACTERIAL POLYSACCHARIDES IN APROTIC SOLVENTS

[75] Inventors: Ralph Calabria, East Brunswick; Frederick W. Hartner, Somerville, both of N.J.; John T. Sisko, Lansdale, Pa.

[73] Assignee: Merck & Co., Inc., Rahway, N.J.

[21] Appl. No.: 353,987

[22] Filed: May 19, 1989

[51] Int. Cl.⁵ .............. C07H 1/00; C07G 17/00; C08B 37/00; A61K 31/00
[52] U.S. Cl. ........................... 514/54; 536/124; 536/1.1
[58] Field of Search ............ 514/54; 536/124, 1.1

[56] References Cited

U.S. PATENT DOCUMENTS

| | | | |
|---|---|---|---|
| 3,883,505 | 5/1975 | Hamuro | 536/124 |
| 4,695,624 | 9/1987 | Marburg et al. | 536/1.1 |
| 4,830,852 | 5/1989 | Marburg et al. | 536/1.1 |
| 4,882,317 | 11/1989 | Marburg et al. | 536/55.1 |

OTHER PUBLICATIONS

Egan et al., J. Am. Chem. Soc 104: 2898–2910 (1982).

*Primary Examiner*—Ronald W. Griffin
*Assistant Examiner*—Everett White
*Attorney, Agent, or Firm*—Jack L. Tribble; Richard S. Parr; Hesna J. Pfeiffer

[57] ABSTRACT

A process for rendering a bacterial polysaccharide soluble in aprotic solvents by exchanging the calcium counterion of a polysaccharide calcium salt for tetra-n-alkylammonium ion by precipitation.

6 Claims, No Drawings

PROCESS FOR SOLUBILIZING POLYANOINIC BACTERIAL POLYSACCHARIDES IN APROTIC SOLVENTS

BACKGROUND OF THE INVENTION

It is often advantageous to solubilize polysaccharides in aprotic solvents to carry out reactions that would not be possible in protic media. Such reactions include those which activate polysaccharides using a reagent that is sensitive to water.

Marburg et al., U.S. Pat. No. 4,695,624, describes the functionalization of polysaccharides for conjugation to proteins in order to prepare polysaccharide-protein conjugates, which are useful as vaccines. The polysaccharides must be covalently-modified prior to conjugation by first solubilizing them in aprotic (non-hydroxylic) solvents so that nucleophilic hydroxyl groups of the polysaccharides can react with electrophilic reagents.

Egan, et al. J. Amer. Chem. Soc.. 1986, 108, 5282–5287 describes the adipic acid dihydrazide (AAD) functionalization of bacterial polysaccharide termini with a carbodiimide. A similar reaction with AAD-functionalized proteins would provide polysaccharide-protein conjugates, which also may be useful as vaccines. In order to avoid competing cyclophosphate formation from the O-phosphoryl isourea intermediate, the reaction must be carried out in aprotic media. AAD is a more reactive nucleophile in aprotic solvents than in water, and can effectively compete with intramolecular cyclization.

Previously, the solubilization of polyanionic bacterial polysaccharides in aprotic solvents was achieved by replacement of the alkali metal or alkali-earth metal cations with large hydrophobic cations such as tri- or tetraalkylammonium, 1-azabicyclo-[2.2.2]-octane, and 1,8-diazabicyclo[5.4.0]undec-7-ene. Solubilization was preferably accomplished by passing the polysaccharide through a strong acid cation exchange resin in the tetralkylammonium form.

Solubilizing polysaccharides according to the method described in Marburg et al., and Egan et al., i.e. by passing the polysaccharide through a strong acid cation exchange resin, requires extensive processing time, numerous operations and large quantities of raw material. In addition, yields suffer because of binding of the polysaccharides to the resin.

A purpose of the present invention is to provide an efficient process for solubilizing polysaccharides in aprotic solvents, using precipitation as the means for cation exchange rather than passage through a cation exchange resin. Precipitation increases yield, and reduces processing time, the number of operations and the amount of raw material required to obtain a given amount of solubilized polysaccharide.

SUMMARY OF THE INVENTION

The present invention is a simple, efficient process for solubilizing polyanionic bacterial polysaccharides such as polyribosylribitol phosphate (PRP) in aprotic solvents. Polysaccharides solubilized in aprotic solvents are particularly suited for conjugation to proteins.

The process takes advantage of the fact that polyanionic bacterial polysaccharides are often isolated as their calcium salts. The process renders bacterial polysaccharides soluble in aprotic solvents by exchanging the calcium counterion of a polysaccharide calcium salt for tetra-n-alkylammonium ion, preferably, tetra-$(C_1-C_{12})$ alkylammonium ion, more preferably tetra-n-butylammonium ion.

The exchange is accomplished by reaction of the polysaccharide with an acid, preferably oxalic, that forms an insoluble salt with calcium. The solution of polysaccharide is then titrated with tetra-n-alkylammonium hydroxide to give the tetra-n-alkylammonium polysaccharide salt. Alternatively, the acid and tetra-n-alkylammonium hydroxide are pre-mixed, and the tetra-n-alkylammonium polysaccharide salt is obtained directly. The precipitate of the insoluble calcium salt is removed by centrifugation or filtration. A solution of the tetra-n-alkylmmonium polysaccharide salt in an aprotic solvent is obtained by lyophilization to remove water and dissolution of the solid in the aprotic solvent, or, preferably, by displacement with the aprotic solvent by distillation.

In one embodiment of the invention, polysaccharide is solubilized in an aprotic solvent by adding an aqueous solution of a calcium salt of a polysaccharide to a suitable amount of aqueous oxalic acid, adjusting the pH of the resulting mixture to about 7 with the addition of a tetra-n-alkylammonium hydroxide to replace the calcium counterion with tetra-n-alkylammonium ion and enhance solubility of the polysaccharide in aprotic solvents, removing the calcium oxalate, and replacing the water with the aprotic solvent.

In an alternative embodiment, polysaccharide is solubilized in an aprotic solvent by adding a suitable amount of an aqueous solution of tetra-n-alkylammonium salt, adjusted to a pH of about 4 with an appropriate acid, to an aqueous mixture of a calcium salt of a polysaccharide, adjusting the pH of the resulting mixture to about 7 with tetra-n-alkylammonium hydroxide to replace the calcium counterion with tetra-n-alkylammonium ion and enhance solubility of the polysaccharide in aprotic solvents, removing the precipitate, and replacing the water with the aprotic solvent.

In another alternative embodiment, polysaccharide is solubilized in an aprotic solvent by adding a suitable amount of an aqueous solution of tetra-n-alkylammonium salt, adjusted to a pH of about 7 with an appropriate acid or salt, to an aqueous mixture of a calcium salt of a polysaccharide to replace the calcium counterion with tetra-n-alkylammonium ion and enhance solubility of the polysaccharide in aprotic solvent, removing the precipitate, and replacing the water with the aprotic solvent.

DETAILED DESCRIPTION OF THE INVENTION

Polysaccharides that can be solubilized in aprotic solvents by the process of the invention may be any bacterial polysaccharides with acid groups. Teichoic acid-like polysaccharides and those containing neuraminic acid with a free carboxyl group are representative but not limiting types. Examples of such bacterial polysaccharides include Streptococcus pneumoniae (pneumococcal) types 6A, 6B, 10A, 11A, 13, 17F, 18C, 19A, 19F, 20, 22F, and 23F, polysaccharides; Group B Streptococcus types Ia, Ib, II and III; Haemophilus influenzae (H. flu) types a, b, c and f polysaccharide; Neisseria meningitidis (meningococcal) groups A, B, C, X, Y, Z, W135 and 29E polysaccharides; and Escherichia coli K1, K12, K13, K92 and K100 polysaccharides.

These polysaccharides, after their purification from the bacterial fermentation broth, may be isolated as their calcium salts. These salts, however, have poor solubility in aprotic solvents. In order to render the polysaccharide soluble in aprotic solvents, the calcium counterion must be exchanged for a hydrophobic one. In the process of this invention, the exchange of the calcium counterion is achieved by precipitation.

In the process, the polysaccharide is treated with any reagent that forms an insoluble calcium salt. The reagent may be an acid, in which case a polysaccharide free acid would be formed and would require neutralization with a hydroxide base that had a hydrophobic cation. Alternatively, the reagent may be salt of a hydrophobic cation, in which case a polysaccharide salt with a hydrophobic counterion would be formed directly. Examples of such insoluble calcium salts include, but are not limited to, calcium fluoride, calcium oxalate, calcium tartrate, calcium carbonate, and calcium tungstate. The preferred insoluble salt is calcium oxalate.

Hydrophobic cations that render the polysaccharide soluble in aprotic solvents include, but are not limited to, tri- or tetra-($C_1$- to $C_{12}$) alkylammonium, 1-azabicyclo[2.2.2]octane, and 1,8-diazabicyclo[5.4.0]undec-7-ene. Preferably the hydrophobic cation is tri- or tetra-($C_1$ to $C_5$) alkylammonium, more preferably tetra-n-butylammonium ion.

The insoluble calcium salt may be separated by centrifugation or filtration. The resulting aqueous solution of polysaccharide is then lyophilized to remove water and the polysaccharide is redissolved in an aprotic solvent. Alternatively, the water is replaced directly with the aprotic solvent by distillation. Suitable solvents include dimethylformamide, dimethylsulfoxide, dimethylacetamide, formamide, and 1,3-dimethyl-2-imidazolidinone, and other similar polar, aprotic solvents, preferably dimethylformamide.

The following examples are provided to further describe the invention, but should not be interpreted as limiting its scope.

EXAMPLE 1

Materials used for this preparation include 6.0 g of polyribosylribitol phosphate (PRP) derived from *Haemoohilus influenzae* type b, 0.978 g of oxalic acid dihydrate, 40% tetra-n-butylammonium hydroxide, dimethylformamide, and pyrogen-free water.

A one liter round bottom flask, equipped with magnetic stirrer, was charged with 180 ml of water, followed by 6.0 g of PRP. While the PRP was dissolving, a solution of 0.978 g of oxalic acid in 49 ml of water was prepared in a one liter three neck round bottom flask. When dissolution of the PRP was complete (about one hour), the PRP was added to the oxalic acid over 20 minutes with a 500 ml addition funnel. The flask that had contained the PRP was washed twice with 10 ml of water, and the washes were also added to the three neck flask.

A 10% solution of tetra-n-butylammonium hydroxide was prepared from the commercial 40% solution by dilution of 15 ml of the 40% solution with 45 ml of water. The pH of the PRP oxalic acid mixture was adjusted to 7.0 with the 10% tetra-n-butylammonium hydroxide. After a 5 minute age, the precipitate of calcium oxalate was removed by filtration through a 600 ml sintered glass funnel. The funnel was washed twice with 20 ml of water, and the washes were combined with the filtered PRP salt.

The filtered PRP salt was charged to a two liter round bottom flask, and the flask was cooled until the solution temperature dropped to 9° C. Two hundred ten ml of dimethylformamide (DMF) was added to the flask. The water was removed by vacuum distillation with a Brinkman model R110 Rotavapor. When the volume of solution in the two liter flask was approximately equal to the volume of DMF charged, the distillation was stopped and another charge of DMF equal in volume to the first addition was added to the flask. This was repeated for four flushes, at which point the concentration of water in the DMF was 0.024 mg/ml, as measured with a Photovolt model Aquatest IV Karl Fisher titrator.

The resulting PRP tetra-n-butylammonium salt is suitable for use as a source of polysaccharide for polysaccharide-protein conjugates prepared and described by Marburg, et. al., U.S. Pat. No. 4,695,624. Such conjugates are prepared by activating the PRP, dissolved in dimethylformamide, with carbonyl diimidazole, a water-sensitive reagent. The activated PRP is functionalized by adding a small appendage with a terminal bromine group, which serves as a reactive site later in the conjugation process. The protein is functionalized by adding a small appendage with a terminal thiol group. When these functionalized molecules are combined, the thiol group displaces the bromine, and a stable covalently bonded conjugate is obtained.

EXAMPLE 2

Material used for this preparation include 1 g of PRP, 163 mg of oxalic acid dihyrate, 40% tetra-n-butylammonium hydroxide, dimethylformamide, and pyrogen-free water.

One gram of PRP was dissolved in 30 ml of water in a beaker. While the PRP was dissolving, a solution of oxalic acid in 11 ml of water was prepared, and the pH was adjusted to about 4 with 20% and 2% tetra-n-butylammonium hydroxide, prepared from the commercial 40% solution. When dissolution of the PRP was complete, the PRP solution was added to the oxalate solution. The pH of the resulting mixture was then adjusted to about 7 with 20% and 2% tetra-n-butylammonium hydroxide. The precipitate of calcium oxalate was removed by filtraion through a 150 ml sintered glass funnel, and the funnel was washed twice with water. The water was replaced with dimethylformamide as described in Example 1.

EXAMPLE 3

Materials used for this preparation include 100 mg of *Neisseria meningitidis* Group C polysaccharide, oxalic acid dihyrate, tetra-n-butylammonium hydroxide, prepared as described in Example 1, dimethylformamide, and pyrogen-free water.

A small beaker was charged with 3 ml of water and 100 mg of Group C polysaccharide. The resulting solution was added dropwise to a solution of 16 mg of oxalic acid in 2 ml of water. The pH of the mixture was adjusted to 7.0 with the tetra-n-butylammonium hydroxide. After a five minute age, the calcium oxalate was removed by filtration through a sintered glass funnel. Five ml of DMF was added to the filtrate and the water was removed by vacuum distillation using a Rotavapor, as described in Example 1.

What is claimed is:

1. A process for solubilizing polysaccharide in an aprotic solvent comprising:
   (a) adding an aqueous solution of a calcium salt of a polysaccharide to a suitable amount of aqueous oxalic acid;

(b) adjusting the pH of the resulting mixture of step (a) to about 7 with addition of a tetra-n-alkylammonium hydroxide to replace the calcium counterion with tetra-n-alkylammonium ion and enhance solubility of the polysaccharide in aprotic solvents;

(c) removing calcium oxalate from solution; and (d) replacing the water with the aprotic solvent.

2. A process of claim 1 wherein the tetra-n-alkylammonium hydroxide is tetra-n-butylammonium hydroxide, and tetra-n-alkylammonium ion is tetra-n-butylammonium ion.

3. A process for solubilizing polysaccharide in an aprotic solvent comprising adding a suitable amount of an aqueous solution of tetra-n-alkylammonium salt at a pH of about 7 to an aqueous mixture of a calcium salt of a polysaccharide to replace the calcium counterion with tetra-n-alkylammonium ion and enhance solubility of the polysaccharide in aprotic solvents, removing precipitate, and replacing the water with the aprotic solvent.

4. A process for solubilizing polysaccharide in an aprotic solvent comprising adding a suitable amount of an aqueous solution of tetra-n-alkylammonium salt at a pH of about 4 to an aqueous mixture of a calcium salt of a polysaccharide, adjusting the pH of the resulting mixture to about 7 with tetra-n-alkylammonium hydroxide to replace the calcium counterion with tetra-n-alkylammonium ion and enhance solubility of the polysaccharide in aprotic solvents, removing precipitate, and replacing the water with the aprotic solvent.

5. A process of claims 3 or 4, wherein the tetra-n-alkylammonium salt is tetra-n-butylammonium salt, and tetra-n-alkylammonium ion is tetra-n-butylammonium ion.

6. A process of claim 5 wherein the tetra-n-butylammonium salt is selected from the group consisting of tetra-n-butylammonium oxalate tetra-n-butylammonium carbonate, tetra-n-butylammonium tungstate, tetra-n-butylammonium tartrate and tetra-n-butylammonium fluoride.

* * * * *